(12) United States Patent
Samproni

(10) Patent No.: US 7,384,523 B2
(45) Date of Patent: Jun. 10, 2008

(54) CHLORIDE ION SELECTIVE MEMBRANE AND SENSOR

(75) Inventor: Jennifer Samproni, Cardiff, CA (US)

(73) Assignee: Radiometer Medical ApS, Copenhagen (DK)

( * ) Notice: Subject to any disclaimer, the term of this patent is extended or adjusted under 35 U.S.C. 154(b) by 723 days.

(21) Appl. No.: 10/617,337

(22) Filed: Jul. 10, 2003

(65) Prior Publication Data

US 2005/0006253 A1    Jan. 13, 2005

(51) Int. Cl.
*G01N 27/333*    (2006.01)

(52) U.S. Cl. ........................ 204/418; 205/789

(58) Field of Classification Search ................ 205/789; 204/416–418
See application file for complete search history.

(56) References Cited

U.S. PATENT DOCUMENTS

| | | | |
|---|---|---|---|
| 4,629,744 A | 12/1986 | Uematsu et al. | 521/62 |
| 5,421,983 A | 6/1995 | Slack et al. | 204/418 |
| 5,531,870 A | 7/1996 | Cha | 205/778 |
| 5,985,117 A | 11/1999 | Bachas et al. | 204/418 |
| 6,015,480 A | 1/2000 | Craig et al. | 204/418 |
| 6,340,714 B1 | 1/2002 | Ghahramani et al. | 521/88 |

FOREIGN PATENT DOCUMENTS

| | | |
|---|---|---|
| EP | 0 653 630 A2 | 5/1995 |
| JP | 4-340454 | 11/1992 |
| JP | 5-60724 | 3/1993 |
| WO | WO 2005/005975 A1 | 1/2005 |

*Primary Examiner*—Alex Noguerola
(74) *Attorney, Agent, or Firm*—Morgan, Lewis & Bockius LLP

(57) ABSTRACT

A chloride selective electrode membrane comprises a polymeric matrix wherein the matrix comprises an epoxy resin, and an amine agent selected from the group consisting of polyamides, amidoamines and mixtures thereof. The amine agent is present in stoichiometric excess and functions as both curing agent and chloride selective agent.

21 Claims, No Drawings ental response. With respect to chloride selective membrane electrodes, a particularly difficult challenge is achieving high selectivity over ions like salicylates (in blood and urine) and/or other similar ions and maintaining this selectivity during repeated exposure of the electrode to interfering substances.

CHLORIDE ION SELECTIVE MEMBRANE AND SENSOR

FIELD OF THE INVENTION

The present invention relates to chloride selective membranes and pertains more particularly to a chloride ion selective electrode having a membrane comprising an epoxy resin and an amine agent selected from polyamides, amidoamines and mixtures thereof.

BACKGROUND OF THE INVENTION

Ion-selective electrodes (ISEs) are widely used to measure the concentration of ions in fluids. Such electrodes have been employed in a wide variety of potentiometric determinations including, for example, determination of the fluoride ion in drinking water and determination of various electrolytes in biological fluids. For example, ISEs are routinely used to determine sodium, calcium, magnesium, potassium, lithium and chloride ions in serum.

Generally, ion selective electrodes are composed of an ion selective membrane, an internal electrolyte solution and an internal reference electrode. An external reference electrode used in conjunction with the ion selective electrode is typically a metal/metal halide electrode such as Ag/AgCl. An ion selective electrode and an external reference electrode comprise a potentiometric cell assembly. Selective transfer of the ion of interest from the sample solution to the ion selective electrode membrane produces an electrical response. The mathematical expression which relates the potential difference across the membrane to the difference in activity is defined by the Nernst Equation, whereas the magnitude of the response is defined as sensitivity. The measured potential difference (ISE versus outer reference electrode potentials) is linearly dependent on the logarithm of the activity of a given ion in solution, and can be used to quantify the ion under investigation. If the membrane's sensitivity does not remain constant during repeated exposure to sample fluids, inaccurate or spurious measurements will be produced and the membrane electrode will have limited use life.

Ion selective electrode membranes are typically formed from a plasticized polymer matrix which contains an ionophore selective for the ion of interest. Many attempts have been made to determine chloride ion in fluid samples using chloride selective electrode membranes. A specific example of such a membrane consists of a polymer, such as polyvinylchloride, an ionophore or ion selective component such as a quaternary ammonium compound and a plasticizing agent for imparting ion motility to the membrane. Quaternary ammonium and phosphonium compounds are frequently employed as ionophores for chloride selective membrane electrodes. Examples of such compounds include tridodecylmethylammonium chloride and tetradodecylammonium chloride. Generally, such chloride selective components are chosen for their lipophilic properties which contribute to enhanced membrane life. Unfortunately, fluids in contact with the membrane can extract plasticizers and ionophores out of the membrane causing the sensitivity of the membrane to be compromised. This is particularly problematic when heparinized plasma samples are analyzed because heparin has been found to adversely affect the membrane. This adverse effect may be due to extraction of ionophore or contamination of the membrane surface with protein which severely limits the use life of the electrode.

Use life of an electrode is generally defined as the amount of exposure required to cause the sensitivity to fall below 60% Nernstian.

Another requirement of a chloride selective electrode is that it has a minimal response to substances other than the analyte of interest. This characteristic is known as selectivity. Sample fluids often contain substances which interfere with the electrode membrane thereby producing a spurious electrical response. With respect to chloride selective membrane electrodes, a particularly difficult challenge is achieving high selectivity over ions like salicylates (in blood and urine) and/or other similar ions and maintaining this selectivity during repeated exposure of the electrode to interfering substances.

As is evident from the foregoing, degradation in the sensitivity and selectivity of a chloride selective membrane electrode as a result of repeated exposure to samples containing interfering substances, as well as the analyte of interest, remains a significant problem. In addition, extending the use life of chloride sensitive membrane electrodes by increasing the stability of membrane selectivity without adversely affecting the sensitivity presents significant challenges.

SUMMARY OF THE INVENTION

An object of the present invention is to provide a chloride selective membrane electrode with stable sensitivity and good selectivity over interfering anions. It is a further object of the invention to provide a chloride selective membrane electrode which possesses a long use life.

To attain the above mentioned objectives, the present invention in a first aspect provides a chloride selective electrode membrane comprising a polymeric matrix wherein the matrix comprises an epoxy resin and an amine agent. The agent is selected from polyamides, amidoamines and mixtures thereof. Present in stoichiometric excess, the amine agent present functions as chloride ion exchanger or chloride ion selective agent as well a curing agent. Use of the amine agent as the chloride ion selective agent eliminates the need to employ additional chloride ionophores or chloride ion exchange agents such as quaternary ammonium compounds.

In a second aspect, the present invention provides a chloride selective electrode which comprises a chloride selective electrode membrane according to the present invention.

In a further aspect, the present invention provides a system for measuring chloride ion in a fluid, wherein the system comprises a chloride selective electrode of the present invention, a reference electrode and means for measuring the electromotive force between the chloride selective electrode and the reference electrode.

In a still further aspect, the present invention provides a sensor assembly for determining chloride ion in a fluid sample. The assembly comprises an electrically insulated substrate having a surface with a reference electrode and a chloride selective electrode formed thereon. The chloride selective electrode comprises a chloride selective electrode membrane comprising a polymeric matrix wherein the matrix comprises an epoxy resin and an amine agent selected from the group consisting of polyamides, amidoamines and mixtures thereof and wherein the amine agent is present in stoichiometric excess. The assembly further comprises means positioned on the surface of the substrate defining a reference flow channel and a sensor flow channel. The reference flow channel is provided with means for passing test liquids over the reference electrode and the sensor flow channel is provided with means for passing test liquids over the sensor electrode. Together, the reference and sensor flow channels define a common outlet for removing liquids from the assembly.

In another aspect, the present invention provides a chloride selective electrode membrane comprising a polymeric matrix wherein the matrix comprises an epoxy resin and an amine agent, wherein the agent is present in the matrix in a stoichiometric excess of at least 150%.

DETAILED DESCRIPTION OF THE INVENTION

The chloride selective electrode of the present invention has a membrane which comprises a polymeric matrix comprising an epoxy resin and a amine agent selected from the group consisting of polyamides, amidoamines and mixtures thereof. A stoichiometric excess of amine agent is employed in the membrane. The electrode further comprises an electrical conductor and is useful for the potentiometric determination of the chloride ion in fluid samples including, but not limited to, biological samples such as blood, urine, plasma, perspiration, spinal fluid and serum.

Biological samples as well as other aqueous samples often contain substances which interfere with the determination of the chloride ion. For example, interference with the determination of the chloride ion due to the presence of salicylate is very troublesome. This is particularly significant in view of the number of individuals on aspirin therapy. Additionally, repeated contact of the electrode membrane with fluid samples often extracts the ionophore or ion exchanger, i.e. the chloride sensing agent, causing the sensitivity of the electrode to be affected. Finally, deposition of substances such as proteins on the surface of the electrode membrane drastically reduces the use life of the electrode. These problems are reduced or eliminated in the present invention which is directed to a chloride sensitive electrode having a membrane comprising an epoxy resin and an amine agent that functions as both chloride ion exchanger or chloride ion selective agent and curing agent for the epoxy resin.

The term "ion selective electrode" (ISE) refers to a potentiometric electrochemical sensor, the potential of which is related to the activity of an ion of interest in a fluid sample. Generally, the potential is linearly dependent on the logarithm of the activity of the ion of interest where activity is defined as the concentration of the ion multiplied by an activity coefficient, where the coefficient is known or available in the art.

The ion of interest in the present invention is the chloride ion, hence the terms "chloride selective electrode membrane "and chloride selective electrode."

A general discussion of the principles of potentiometric ion sensors is provided by Oesch et al., "Ion Selective Membranes for Clinical Use," Clinical Chemistry, Vol. 32, No. 8, pp 1448-1459 (1986) and by Burnett et al, "Use of Ion Selective Electrodes for Blood-Electrolyte Analysis" Clin. Chem. Lab Med. Vol. 38, No. 4, pp 363-370 (2000) and the International Union of Pure and Applied Chemistry (IUPAC) Analytical Compendium, Chapter 8, Section 3.2.1, "General Terms Related to Ion Selective Electrodes."

The epoxy resin utilized in the present invention can be any epoxy resin which can be cured by amine agents employed herein. Generally, the epoxy resin can be any curable epoxy resin having a 1,2-epoxy equivalency greater than one and preferably, on the average, more than about 1.5 epoxide groups per molecule. The epoxy resin can be saturated or unsaturated, linear or branched, aliphatic, cycloaliphatic, aromatic or heterocyclic, and may bear substituents which do not materially interfere with the curing reaction. Suitable epoxy resins are those produced by the reaction of a polyhydric alcohol or phenol with excess epichlorohydrin under basic conditions such as in an alkaline reaction medium or in the presence of a suitable base. Preferably the epoxy resin is a polyglycidyl ether of a polyhydric phenol. Examples of suitable polyhydric phenols include: 2,2-bis(4-hydroxyphenyl) propane (bisphenol-A); 2,2-bis(4-hydroxy-3-tert-butylphenyl) propane; 1,1-bis(4-hydroxyphenyl) ethane; 1,1-bis(4-hydroxyphenyl) isobutane; 1,1-bis(4-hydroxy-3-alkylphenyl) ethane and the like. Suitable dihydric phenols can also be obtained from the reaction of phenol with aldehydes such as formaldehyde (bisphenol-F). Commercial examples of preferred epoxy resins that can be advantageously employed in the present invention include, for example, EPON® epoxy resins available from Resolution Performance Products, DER® epoxy resins available form Dow Chemical Company and Araldite® epoxy resin available from Ciba Geigy.

Specific examples of epoxy resins include EPON® epoxy resin 828, DER® epoxy resin 331 and Araldite® epoxy resin GY 60202. The general structure of these polyglycidyl ether resins consists of epoxide groups at each end and a repeat unit in the middle. Because of the varying number of repeat units which can be incorporated into the resin, varying viscosities can be obtained The epoxy resins utilized in the present invention are cured using a amine agent selected from the group consisting of polyamides, amidoamines and mixtures thereof. The amine agent functions as both a curing agent and a weak base-type anion exchanger, i.e. a chloride selective agent. The active ion exchange sites are the secondary (—NHR) and tertiary (—NRR) amino groups present in the amine agent.

Polyamides that may be utilized in the present invention are the reaction product of unsaturated fatty acid dimer and polyalkylene amines such as diethylene triamine (DETA), triethylene tetramine (TETA) and tetraethylene pentamine (TEPA). Unsaturated fatty acids that may be used in the preparation of fatty acid dimer include, but are not limited to C18 unsaturated fatty acids such as oleic acid, linoleic acid, linolenic acid and the like. EPIKURE® 3140 curing agent available form Resolution Performance Products is representative of a class of commercial polyamide curing agents that may be used in the present invention.

A process for dimerizing monounsaturated fatty acids such a oleic acid and polyunsaturated fatty acids such as linoleic acid and linolenic acid has been described in U.S. Pat. No. 2,793,220 assigned to Emery Industries. Commercially available acid dimer derived from various oils including tall oil, castor oil, linseed oil, soybean oil and the like can also be used in the present invention. Tall oil fatty acids are primarily a mixture of palmitic acid, acid, stearic acid, oleic acid and linoleic acid. These unsaturated tall oil fatty acids are used to produce crude dimer which, when distilled, removes most of the monomer leaving standard acid dimer. Further distillation produces distilled acid dimer and acid trimer.

Amidoamines utilized in the present invention are the reaction product of monomeric or monofunctional saturated and unsaturated fatty acids and polyalkylene amines including DETA, TETA, TEPA and the like. Fatty acids that may be utilized in the preparation of amidoamines of the invention include, but are not limited to palmitic acid, stearic acid oleic acid, linoleic acid, linolenic acid and the like. EPIKURE® curing agent 3055 from Resolution Performance Products is representative of a commercially available amidoamine curing agent that may be advantageously employed herein.

Amide groups present in the polyamides and amidoamines employed herein can undergo intra-molecular reaction with residual amino groups thereby forming cyclic structures. The most common cyclic structure to form is the imidazoline structure. Cyclization is accomplished by means of a high reaction temperature that converts the open amide structure to a cyclic structure. The reaction is reversible and amide groups may be recovered in the presence of water. The advantage of having imidazoline groups present in the amine agents employed herein is that curing of the epoxy resin is slowed down providing for a longer pot life and easier fabrication of articles.

The invention requires that a stoichiometric excess of amine agent be employed in the chloride selective membrane of the invention. Stoichiometric excess is the excess of agent employed over the amount of agent required for complete curing of the epoxy resin. When the agent is a polyamide, the term "stoichiometric excess" refers to an amount of polyamide that exceeds stoichiometry by about 150% to about 700%. Preferably, the amount of polyamide exceeds stoichiometry by about 160% to about 220%. In the most preferred embodiment, the amount of polyamide exceeds stoichiometry by about 200%. When the amine is an amidoamine, the term "stoichiomeric excess" refers to an amount of amidoamine that exceeds stoichiometry by about 150% to about 250%.

The chloride selective membrane of the invention can be prepared by mixing a suitable amount of an epoxy resin and a suitable amine agent selected from polyamides and amidoamines as described herein with an appropriate solvent to produce chloride selective compositions of the invention. The solvent employed can be any solvent commonly used to prepare conventional membranes and can include, for example tetrahydrofuran, cyclohexanone, xylene, toluene and the like. Generally, the chloride selective compositions of the invention which are to be applied by a dispensing technique contain from about 10% to about 50% by weight solids.

The epoxy resin compositions of the invention can also contain adhesion promoters including, but not limited to, clays, silicas, silicates and mixtures thereof. For example, the chloride such silicates or silicas utilized in the present invention contain talc and fumed silica. Fumed silica treated to render it hydrophobic may advantageously be employed in the present invention. Utilization of such hydrophobic particles can significantly reduce adhesion and/or deposition of protein on the electrode membrane.

In the event additional chloride selective agent is desired in the compositions of the invention, additional ionophore or ion exchange agents may be added. For example, quaternary ammonium or phosphonium compounds such as tridodecylmethylammonium chloride and tetradecylammonium chloride may be employed. Notwithstanding the foregoing, the polyamide and/or amidoamine agents employed herein function very effectively as chloride selective agents without the addition of any other ionophore or ion exchange agent.

Particular advantages of the chloride selective membranes of the invention over other chloride selective membranes include high sensitivity obtained without the addition of other ionophores or ion exchange agents which may migrate out of the membrane, thereby reducing the use life and contaminating downstream sensors. In the chloride selective membranes of the invention, the chloride selective agent is the amine curing agent which serves as an ion exchanger covalently bound to the epoxy resin matrix thereby further extending the use life of the membrane.

The chloride selective agent normally has a limited capacity for the exchange of chloride ions. Therefore, it is particularly advantageous to have the largest degree of surplus amine available. In the present invention, the use life is significantly extended when the amine agent is present in the matrix in a stoichiometric excess of at least 150%.

Furthermore, the addition of silica or silicates to the chloride selective membranes according to the invention reduces the interference from other anions, particularly interference from bicarbonate ions, reduces the oxidation of the Ag/AgCl contact on the substrate by the amine, and inhibits the adhesion of protein to the membrane surface.

Finally, the chloride selective membranes of the invention exhibit improved selectivity over prior art chloride selective membranes. This occurs because of the elimination of lipophilic ion exchanger agents such as tridecylmethylammonium chloride in the present invention. Such ion exchange agents are typically used in conventional chloride electrode membranes.

Having thus described specific embodiments of the present invention, is should be noted by those skilled in the art that the disclosures herein are exemplary only and that various other alternatives, adaptations, and modifications may be made within the scope of the present invention.

The following examples serve to illustrate the present invention.

EXAMPLE 1

Calculation of the stoichiometric mix ratio by weight of curing agent, i.e. amine agent, to epoxy resin is performed as outlined below.

First, the equivalent weights of the epoxy resin and the amine agent are obtained using, for example, the average equivalent weight range listed in the product literature Resin: EPON® 828 epoxy resin Eq. wt. = 190 g/eq Amine agent: EPICURE® 3140 curing agent Eq. wt. = 95 g/eq Next, parts of amine agent required to cure 100 parts of resin, referred to as phr is determined as follows:

$$Phr = \frac{\text{Amine eq. wt.}}{\text{Resin eq. wt.}} \times 100 \text{ parts resin} = \frac{95}{190} \times 100 = 50.$$

Based on the foregoing, the stoichiometric mix ratio by weight=50 parts of amine agent per 100 parts epoxy resin.

The present invention however requires that the amine agent be present in stoichiometric excess. The term, as used herein, is defined as the excess of agent employed over the amount of agent required for complete curing of the epoxy resin. Accordingly, the phr value calculated above is increased to a value that exceeds stoichiometry. When the amine agent employed is a polyamide, the amount of polyamide employed exceeds stoichiometry by about 150% to about 700%. Preferably the amount of polyamide exceeds stoichiometry by about 160% to about 220%. When the amine agent employed is an amidoamine, the amount of amidoamine exceeds stoichiometry by about 150% to about 250%.

EXAMPLE 2

Preparation of Chloride Ion Selective Membrane Material

Into a 100 milliliter (ml) beaker containing 32 grams (g) of epoxy resin (Epon 828, available from Resolution Performance Products) was added 19 g of talc (Nytal 100, available from R. T. Vanderbilt). The resulting mixture was then stirred to a homogenous state.

Into a 100 milliliter (ml) beaker containing 48 grams (g) of polyamide curing agent (EpiKure 3140, available from Resolution Performance Products) was added 1.7 g of fumed silica (Cab-o-sil TS720, available from Cabot Corporation). The resulting mixture was then stirred to a homogenous state.

The homogenous epoxy resin mixture was then admixed with the homogenous polyamide mixture for approximately 5 minutes using a spatula. The resulting chloride selective material was subsequently utilized to prepare a chloride selective electrode.

The chloride-selective material was applied to the electrode surface using thick film technique such as screen printing, then cured for 3 hours at 75° C. under ambient conditions.

EXAMPLE 3

Preparation of a Chloride Ion Selective Membrane Material Suitable for Dispensing Into a 100 milliliter (ml) beaker containing 32 grams (g) of epoxy resin (Epon 828, available from Resolution Performance Products), 48 grams (g) of polyamide curing agent (EpiKure 3140, available from Resolution Performance Products) was added. The resulting mixture was then stirred to a homogenous state using a spatula.

The above obtained mixture was dispersed in 48 grains (g) of cyclohexanone and subsequently utilized in preparing a dispensed chloride selective electrode. In this embodiment, the chloride-selective material was applied to the electrode surface using a dispensing technique, then cured under Argon for 24 hours at room temperature, followed by 60 minutes at 65° C. under ambient conditions.

EXAMPLE 4

Preparation of a Chloride Ion Selective Electrode

The chloride selective electrode material prepared as described in Example 2 above was incorporated into a sensor assembly as described below.

A nonconducting ceramic substrate (96% alumina ($Al_2O_3$), ADS-96R, CoorsTek, Grand Junction, Colo., U.S.) was ultrasonically cleaned and dried. A silver pattern serving as a conductor was screen printed onto the ceramic substrate using silver paste QS175 (E. I. du Pont de Nemours and Company, Delaware., U.S.). Other metallic conductors such as gold or platinum are equally suitable. The printed ceramic substrate was then dried in air by placing it in a convection oven at 115° C. for fifteen (15) minutes. Thereafter, the substrate was fired in a thick film conveyor belt furnace such as that commonly used in thick film technology, employing a heating rate of 40° C. per minute up to 850° C. The ceramic substrate was held at 850° C. degree for five (5) minutes and then cooled at a rate of 40° C. per minute. The thickness of the metallic conductor is in the range of 8 µm to 20 µm. The shape of the electrode is circular, with a diameter from 0.028 to 0.046 inches.

One or more layers of thick film dielectric glass ESL (Electro-Science Laboratories, Inc.) 4904 were then screen printed onto the ceramic substrate and dried, leaving the electrode layer, i.e. the metallic conductor exposed. The ceramic substrate containing the dielectric layer was then fired in a thick film belt furnace by employing a heating rate of 40° C. per minute up to 800° C. and held at 800° C. degree. C. for five (5) minutes and then cooled at a rate of 40° C. per minute. The dielectric glass composition was selected to produce good chemical stability in the presence of electrolyte and to contain a vitreous silica phase that is favorable for silane binding with subsequent encapsulating polymeric layers. The thickness of the glass layer is usually in the 6-16 µm range.

A mixture of silver and silver chloride (a ratio of 70% silver and 30% silver chloride by weight) combined with solvents and polymer binder components was then screen printed on the metallic conductor. The specific formulation used was AgCl14 (Polymer Innovations, Inc., San Marcos, Calif.) The ceramic substrate was then cured by heating at 185° C. in a convection oven to for three hours. The thickness of the resulting Ag/AgCl electrode was in the 5-20 µm range. The purpose of the Ag/AgCl electrode is to produce a potentiometric sensor electrode for use with a standard Ag/AgCl reference electrode. Other formulations with an appropriate ratio of Ag/AgCl will produce similar results. The printed diameter of the Ag/AgCl electrode is typically more than 5% larger than the diameter of the metallic conductor so that the metallic conductor is not exposed to the chloride selective membrane.

The above-described layers are typically deposited by standard thick film screen printing.

The sensor assembly containing the chloride selective membrane electrode also has a reference electrode to provide an accurate reference potential supported on the assembly. The reference electrode was constructed in essentially the same way as the chloride selective membrane electrode but does not utilize the outer layer, or the chloride selective membrane layer.

After deposition of the Ag/AgCl layer, a first polymeric layer is deposited on the substrate with openings for the electrodes. The first polymeric layer (together with the dielectric glass layer) forms the lower wall of the sensor cavities in which the electrodes are positioned. The polymer material is screen printable, absorbs minimal moisture, chemically isolates the membrane chemistry within the cavity, and produces a strong bond with the polymeric membrane. The polymer also forms a strong bond with the dielectric glass layer when the sensor is exposed to moisture over long time periods.

Specific polymer used to form the polymeric layers is preferably a composition of 28.1% acrylic resin, 36.4% carbitol acetate, 34.3% calcined kaolin, 0.2% fumed silica, and 1.0% silane, noted in percentage by weight. The acrylic resin is preferably a low molecular weight polyethylmethacrylate, such as Elvacite, part number 2041, available from Lucite International, Inc. Cordova, Tenn., USA. The calcined kaolin is preferably a silaninized kaolin, such as part number HF900, available from Engelhard. The silane is preferably an epoxy silane, such as trimethoxysilane. Silane bonds to the hydroxyl groups on the dielectric glass layer and yet is left with free functional groups to crosslink with the resin's functional groups. In accordance with one embodiment of the present invention, the first polymeric layer is deposited in three screening processes/procedures in order to attain the desired thickness (i.e., preferably approximately 0.0020 inches). Each polymeric layer is dried after each screening process. A second polymeric layer is deposited to form the upper walls of the sensor cavities. The first and second polymeric layer, differ only in the diameter across the cavity at the lower cavity wall and at the upper cavity wall and the number of screening processes that are required to achieve the desired depth. In the case of the second polymeric layer, nine (9) screening procedures were required to attain the desired thickness. Each polymeric layer is dried after each screening procedure. In addition, after the last two procedures, the polymer is both screened and cured. In a preferred embodiment of the present invention, the last screening procedure can be omitted if the second polymeric layer has achieved the desired thickness (i.e., preferably 0.0075-0.0105 inches after curing).

The diameter of the opening in the first polymeric layer is preferably smaller by 5% or more than the diameter of the Ag/AgCl electrode so that the chloride selective membrane is exposed only to the Ag/AgCl electrode and the wall thickness of encapsulating polymer.

The diameter of the sensor cavities is preferably carefully controlled to aid in controlling the deposition of the membrane which is placed over the sensor electrodes. That is, the sensor cavities formed as described herein enable a droplet or printed deposit of chloride selective membrane material to be captured and formed into a centrosymmetric form over the electrode with sufficient surface contact with the walls of the cavity to assure that the membrane remains physically attached.

Preferably, the sensor cavity for the 0.046 inch diameter chloride sensor, has a total depth of approximately $y=0.0075$ inches, a diameter at the upper wall of approximately $x1=0.070$ inches, and at the lower wall of approximately $x2=0.06$ inches. In a preferred embodiment, the diameter $x3$ is equal to 0.078 inches. It is to be understood that a membrane of the same thickness may be produced by increasing the diameter of the sensor cavity and increasing the volumetric quantity of the membrane solution that is applied to the sensor in proportion to the increase in the volume of the cavity. Likewise, the same thickness can be maintained by decreasing the diameter of the sensor cavity and proportionally decreasing the volumetric quantity of the membrane solution. It will be clear that in an alternative embodiment of the present invention, the sensor cavities may have a shape other than the generally cylindrical shape disclosed above. For example, in accordance with one embodiment of the present invention, the electrodes are formed in an oval shape to reduce the required volume of test sample required. However, in a preferred embodiment, the sensor cavities are either cylindrical or generally conical.

Once the sensor cavities have been formed and the polymeric layers cured, the cavity of each sensor is filled with liquid chloride sensitive membrane material by a variant of the screen printing process called stenciling. The stencil is a stainless steel sheet with laser cut apertures of the same diameter as the electrode. The thickness of the stainless steel sheet used is slightly less than the thickness of the inside wall of the sensor cavity. The apertures act as dispensing tips, i.e. they fill with the liquid chloride sensitive membrane material during printing. Following this, the stencil and substrate separate and a portion of the chloride selective membrane material remains on the substrate. The appropriate stencil thickness produces a printed membrane having a height approximately planar to the surface of the substrate. Otherwise a standard screen printing process is used in deposition of the chloride selective membrane material.

The viscosity, or more specifically, the "yield point" of the chloride selective membrane material has been optimized to the "aspect ratio" of the sensor cavity so that the deposit will slump into a rounded deposit that wets the surface of the sensor cavity and flows to fill the sensor cavity.

The sensor assembly is cured at 70° C. in a convection oven for approximately 3 hours. The resulting finished sensor assembly was stored under nitrogen until used.

EXAMPLE 5

An alternative process for deposition of liquid chloride selective membrane material is described below.

Chloride selective polymer material, prepared as described in Example 3, was dispensed onto the ceramic substrate using standard liquid dispensing instrumentation. The dispensed chloride selective polymer material was then cured for 24 hours under Argon at room temperature, then the ceramic substrate at was heated to 65° C. for 60 minutes to form the chloride selective membrane. The resulting ceramic substrate assembly was then exposed to an ultraviolet source at an intensity of 750 millijoules per square centimeter. The cured ceramic substrate assembly was then mounted in a cartridge having an elastomer component which is pressed against the finished ceramic substrate so as to define reference and sensor flow channels respectively thus providing means for reference and sample liquids to flow over the reference and chloride selective electrodes.

An example of a cartridge in which a sensor in accordance with the invention may be used is disclosed in U.S. Pat. No. 6,193,864 which is incorporated herein by reference.

What is claimed is:

1. A chloride selective electrode membrane comprising a polymeric matrix wherein said matrix comprises:
   an epoxy resin curable by an amine agent; and
   an amine curing agent selected from the group consisting of polyamides, amidoamines and mixtures thereof, wherein said amine curing agent is present in stoichiometric excess over the amount required for complete curing of the epoxy resin.

2. A chloride selective electrode membrane according to claim 1, wherein said amine curing agent is a polyamide.

3. A chloride selective electrode membrane according to claim 2 wherein said polyamide is prepared by reacting an acid component and a polyalkylene polyamine component, said acid component comprising an unsaturated fatty acid dimer.

4. A chloride selective electrode membrane according to claim 3 wherein said unsaturated fatty acid dimer comprises a polyunsaturated fatty acid dimer.

5. A chloride selective electrode membrane according to claim 4 further comprising a monounsaturated fatty acid dimer.

6. A chloride selective electrode membrane according to claim 4 wherein said polyunsaturated fatty acid dimer is a C18 polyunsaturated fatty acid dimer.

7. A chloride selective electrode membrane according to claim 5 wherein said monounsaturated fatty acid dimer is oleic acid dimer.

8. A chloride selective electrode membrane according to claim 3 wherein said unsaturated fatty acid dimer is a dimerized fatty acid from an oil selected from tall oil, castor oil, linseed oil, soybean oil and mixtures thereof.

9. A chloride selective electrode membrane according to claim 3 wherein said polyalkylene polyamine component is selected from the group consisting of diethylene triamine, triethylene tetramine and tetraethylene pentamine, and mixtures thereof.

10. A chloride selective electrode membrane according to claim 1 wherein said polymer matrix further comprises an adhesion promoter selected from the group consisting of clays, silicas, silicates and mixtures thereof.

11. A chloride selective electrode membrane according to claim 1, wherein said epoxy resin is prepared by reacting bisphenol A and epichlorohydrin.

12. A chloride selective electrode membrane according to claim 1 wherein the amount of said amine curing agent is present in a stoichiometric excess of at least 150%.

13. A chloride selective electrode membrane according to claim 1 wherein said amine curing agent is an amidoamine.

14. A chloride selective electrode membrane according to claim 13 wherein said amidoamine is prepared by reacting an acid component and an amine component, said acid component comprising monomeric saturated and unsaturated fatty acids.

15. A chloride selective electrode membrane according to claim 14 wherein said amine component is selected from the group consisting of alkylene diamines and polyalkylene polyamines and mixtures thereof.

16. A method of applying the chloride selective membrane material of claim 1 to an inert substrate, said method comprising:
dispensing said material to onto said substrate; and
heating the substrate containing dispensed chloride selective material to obtain chloride selective membrane.

17. A chloride selective electrode which comprises a chloride selective electrode membrane comprising a polymeric matrix, wherein said matrix comprises:
an epoxy resin curable by an amine agent; and
an amine curing agent selected from the group consisting of polyamides, amidoamines and mixtures thereof wherein said amine curing agent is present in stoichiometric excess over the amount required for complete curing of the epoxy resin.

18. A system for measuring chloride ion in a fluid, said system comprising: a chloride selective electrode according to claim 17 a reference electrode; and means for measuring the electromotive force between said chloride selective electrode and said reference electrode.

19. A chloride selective electrode membrane according to claim 17 wherein
said amine curing agent is present in a stoichiometric excess of at least 150%.

20. A method of applying the chloride selective membrane material of claim 19 to an inert substrate, said method comprising:
dispensing said material to onto said substrate; and
heating the substrate containing dispensed chloride selective material to obtain chloride selective membrane.

21. A sensor assembly for determining chloride ion in a test liquid, comprising:
an electrically insulated substrate having a surface with a reference electrode and
a chloride selective electrode formed thereon, wherein the chloride selective electrode comprises:
a chloride selective electrode membrane comprising a polymeric matrix wherein said matrix comprises:
an epoxy resin curable by an amine agent; and
an amine curing agent selected from the group consisting of polyamide, amidoamines and mixtures thereof, wherein said amine curing agent is present in stoichiometric excess over the amount required for complete curing of the epoxy resin;
means positioned on the surface of the substrate defining a reference flow channel and a sensor flow channel;
said reference flow channel having means for passing reference liquids over the reference electrode; said sensor flow channel having means for passing test liquid over the sensor electrode; and said reference and sensor flow channels defining a common outlet for removing liquids from the assembly.

* * * * *